US009751204B2

(12) United States Patent
Blum et al.

(10) Patent No.: US 9,751,204 B2
(45) Date of Patent: Sep. 5, 2017

(54) HAND-HELD POWER TOOL DEVICE

(71) Applicant: Robert Bosch GmbH, Stuttgart (DE)

(72) Inventors: Jens Blum, Filderstadt (DE); Heiko Roehm, Stuttgart (DE); Tobias Herr, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 446 days.

(21) Appl. No.: 14/576,645

(22) Filed: Dec. 19, 2014

(65) Prior Publication Data

US 2015/0101836 A1 Apr. 16, 2015

Related U.S. Application Data

(63) Continuation of application No. 12/951,698, filed on Nov. 22, 2010, now Pat. No. 8,939,232.

(30) Foreign Application Priority Data

Dec. 18, 2009 (DE) ........................ 10 2009 054 929

(51) Int. Cl.
*A61B 17/04* (2006.01)
*A61B 17/10* (2006.01)
*B25F 5/00* (2006.01)
*B25D 16/00* (2006.01)

(52) U.S. Cl.
CPC ............ *B25F 5/001* (2013.01); *B25D 16/003* (2013.01); *B25D 2216/0069* (2013.01)

(58) Field of Classification Search
CPC ............ B25F 5/001; B25D 2216/0069; B25D 16/003
USPC .................................... 173/90, 93, 216, 213
See application file for complete search history.

(56) References Cited

U.S. PATENT DOCUMENTS 4,784,044 A * 11/1988 Klement ............... B23B 31/261 92/23
4,804,048 A 2/1989 Porth
5,016,501 A 5/1991 Holzer
5,984,022 A 11/1999 Harman et al.
6,273,659 B1 * 8/2001 Goto ..................... B24B 45/006 411/354
6,311,787 B1 11/2001 Berry et al.
6,454,020 B1 9/2002 Jong
6,715,562 B1 4/2004 Chen
6,949,110 B2 9/2005 Ark et al.
7,048,107 B1 5/2006 Geis et al.
7,063,201 B2 6/2006 Nakamura et al.
7,073,606 B2 7/2006 Mamber et al.
7,223,163 B2 5/2007 Neumeier et al.
(Continued)

FOREIGN PATENT DOCUMENTS

CN 101058173 10/2007
DE 19942271 3/2001
(Continued)

*Primary Examiner* — Robert Long
(74) *Attorney, Agent, or Firm* — Norton Rose Fulbright US LLP; Gerard Messina

(57) ABSTRACT

The invention is based on a hand-held power tool device equipped with a locking device. The locking device is provided for locking an output device and has at least one locking element for supporting at least one radial clamping force. According to a proposed embodiment, the locking element is provided to fasten and/or axially secure at least one component.

24 Claims, 3 Drawing Sheets

(56) References Cited

U.S. PATENT DOCUMENTS

| | | | |
|---|---|---|---|
| 7,367,757 B2 | 5/2008 | Phillips | |
| 7,506,694 B2 * | 3/2009 | Stirm | B25F 5/00 173/176 |
| 7,900,713 B2 * | 3/2011 | Chen | B23B 45/008 173/178 |
| 7,963,346 B2 | 6/2011 | Brodin | |
| 8,172,003 B2 | 5/2012 | Robieu et al. | |
| 2002/0130007 A1 | 9/2002 | Nakamura et al. | |
| 2002/0153147 A1 | 10/2002 | Mamber et al. | |
| 2003/0184029 A1 * | 10/2003 | McCurry | B23B 31/1253 279/61 |
| 2003/0196824 A1 | 10/2003 | Gass et al. | |
| 2004/0231952 A1 | 11/2004 | Nakamura et al. | |
| 2006/0084370 A1 | 4/2006 | Robieu et al. | |
| 2007/0084616 A1 | 4/2007 | Lam et al. | |
| 2007/0157774 A1 | 7/2007 | Gross et al. | |
| 2007/0181322 A1 * | 8/2007 | Hansson | B25F 5/001 173/217 |
| 2007/0267207 A1 | 11/2007 | Ito | |
| 2008/0087449 A1 | 4/2008 | Lam et al. | |
| 2008/0185793 A1 | 8/2008 | Haimer | |
| 2011/0036609 A1 | 2/2011 | Blickle | |
| 2011/0214892 A1 | 9/2011 | Hecht et al. | |
| 2011/0220380 A1 | 9/2011 | Roehm | |
| 2012/0090863 A1 | 4/2012 | Puzio et al. | |
| 2012/0111594 A1 * | 5/2012 | Herr | B23B 31/1207 173/104 |

FOREIGN PATENT DOCUMENTS

| | | |
|---|---|---|
| EP | 0982101 | 3/2000 |
| EP | 1 652 631 | 5/2006 |
| EP | 1 726 849 | 11/2006 |
| EP | 2 008 773 | 12/2008 |
| GB | 2471373 | 12/2010 |
| JP | 5-269677 | 10/1993 |
| WO | WO 2010/149474 | 12/2010 |

* cited by examiner

HAND-HELD POWER TOOL DEVICE

CROSS-REFERENCE TO RELATED APPLICATION

This application is a continuation application of U.S. patent application Ser. No. 12/951,698, filed on Nov. 22, 2010, which claims priority to and the benefit of German Patent Application No. 10 2009 054 929.3, filed on Dec. 18, 2009, the contents of each of which are hereby incorporated by reference in their entireties.

BACKGROUND OF THE INVENTION

Field of the Invention

The invention is based on a hand-held power tool device equipped with a locking device, which is for locking an output device and has at least one locking element for supporting at least one radial clamping force.

Description of the Prior Art

There is already a known hand-held power tool device, in particular for a screwdriver, equipped with a locking device, which is for locking an output device in the form of a spindle and has a locking element embodied in the form of a clamping ring for supporting radial clamping forces of clamping elements composed of rollers.

SUMMARY AND ADVANTAGES OF THE INVENTION

According to one proposed embodiment, the locking element is provided for fastening at least one component. In this connection, a "locking device" should in particular be understood to be a device that is provided to disable and/or inhibit an output device and/or a rotary motion of the output device in at least one operating state. An "output device" should in particular be understood here to be a device that is provided to transmit a driving power and that preferably has at least one output shaft that a motor drives in an operating state of the hand-held power tool. The term "radial" here should in particular be understood to be radial to a rotation axis of the rotary motion of the output device to be locked. In addition, a "clamping force" should in particular be understood to be a force that is produced by a clamping procedure as part of the locking action. Preferably, the output shaft drives a tool to rotate during operation, for example a screwdriver, a drill, a boring chisel, a milling tool, etc. The term "provided" should in particular be understood to be specially equipped and/or designed. In addition, the term "fastening" should in particular be understood to mean that in the fully assembled state of a hand-held power tool with the hand-held power tool device, the locking element is used for fastening an additional component; the additional component is fixed firmly in place with the locking element and the locking element supports a bearing force of the component. An "axial securing" should in particular be understood to mean that a bearing force of the component, in particular a transmission component, is supported by the locking element in the axial direction, i.e. particularly in the direction of a rotation axis of the output device. The locking element in this case is preferably manufactured at least partially out of a metallic material. Particularly preferably, the locking element is embodied in the form of a screw-mounting flange to which at least one component, in particular a transmission component, can be fastened and/or axially secured by means of a screw connection.

Through a corresponding embodiment, a component—which must have a fundamentally rugged construction—can be advantageously used to support additional bearing forces. It is advantageously possible to reduce mechanical and thermal stresses on housing parts, in particular plastic housing parts. It is also advantageously possible, by fastening an additional component to the locking element, to achieve an advantageous reinforcing of the locking element, allowing the latter to be embodied in a particularly space-saving and light-weight fashion.

The locking element can be composed of various components deemed suitable by the person skilled in the art, e.g. one or more annular segments, etc. It is particularly advantageous, however, for the locking element to be composed of a clamping ring that preferably extends over 360°, advantageously permitting forces to be supported.

If the hand-held power tool device has a housing unit in which the locking element is supported with a radial play of less than 0.1 mm and particularly advantageously, less than 0.05 mm and particularly preferably, in which the locking element is affixed without play in the radial direction, then in particular, bearing forces of the component, which is to be fastened by means of the locking element, can be supported in an advantageously determined fashion, in particular without play.

The locking element can be fastened in a housing unit equipped with fastening elements such as screws, clamping elements, etc. and/or can be pressed-fitted into a housing unit. In a particularly advantageous embodiment, however, the housing unit is molded around the locking element, i.e. in a manufacturing process of the housing unit, the locking element is in particular inserted into an injection mold and then a material of which the housing unit is at least partially manufactured, in particular such as plastic, is injection molded around it. Through a corresponding embodiment, it is possible to achieve an advantageously inexpensive design, particularly in that the locking element can be manufactured within broad tolerances with regard to its outer contour.

According to another proposed embodiment of the invention, the hand-held power tool device has a pivot bearing unit that is provided to support the output device and includes the component to be fastened, which is composed of a bearing component. The term "pivot bearing unit" here should in particular be understood to mean a unit that is provided for the rotating support of a component of the output device and in particular, has at least one slide bearing and/or rolling bearing. Through a corresponding embodiment, it is possible in particular to achieve an advantageous reinforcement of the locking element, advantageously providing savings with regard to space, in particular a length of the installation space, particularly if the bearing component and the locking element are situated in at least one common plane extending perpendicular to a rotation axis of the pivot bearing unit. The bearing component can be fastened to the locking element using various fastening elements deemed suitable by the person skilled in the art, e.g. screws, clamping elements, etc. It is particularly advantageous, however, for the hearing component to he connected to the locking element by means of a press-fitted connection, making it possible to advantageously avoid undesirable tolerances in a structurally simple fashion. In this connection, it is particularly preferable for the bearing component, e.g. a ring element, to be press-fitted into a recess of the locking element.

According to another proposed embodiment, the locking element is provided for axially securing at least one output shaft and/or at least one adjusting element, once again reducing stresses on housing components and enabling savings with regard to components, space, and weight. An “adjusting element” should in particular be understood to be an element that is provided for being actuated by a user and/or an actuator during an adjustment, e.g. when setting of a maximum torque, etc.

According to another proposed embodiment, the locking element is provided for directly supporting an output shaft. The term “directly” here should in particular be understood to mean that the locking element and the output shaft contact each other with corresponding bearing surfaces directly, i.e. without interposed components. With a corresponding embodiment, the locking element—which must have a fundamentally rugged construction—can be advantageously used to directly support a bearing force, thus permitting savings in terms of components, space, weight, and assembly complexity.

If the locking element in this case is manufactured out of a sintered material, particularly advantageous sliding properties can be achieved in a structurally simple fashion.

The embodiment according to the invention, i.e. the hand-held power tool device according to the invention, can be used in various hand-held tools deemed suitable by the person skilled in the art, e.g. in angle grinders, milling machines, power saws, power drills, impact drills, and rotary hammers. The embodiment according to the invention can be used to particular advantage in cordless devices due to the particularly advantageous possibilities for savings in terms of components, space, and weight.

BRIEF DESCRIPTION OF THE DRAWINGS

The invention will be better understood and further objects and advantages thereof will become more apparent from the ensuing detailed description of preferred embodiments taken in conjunction with the drawings, in which.

DESCRIPTION OF THE PREFERRED EMBODIMENTS

Figure 1:
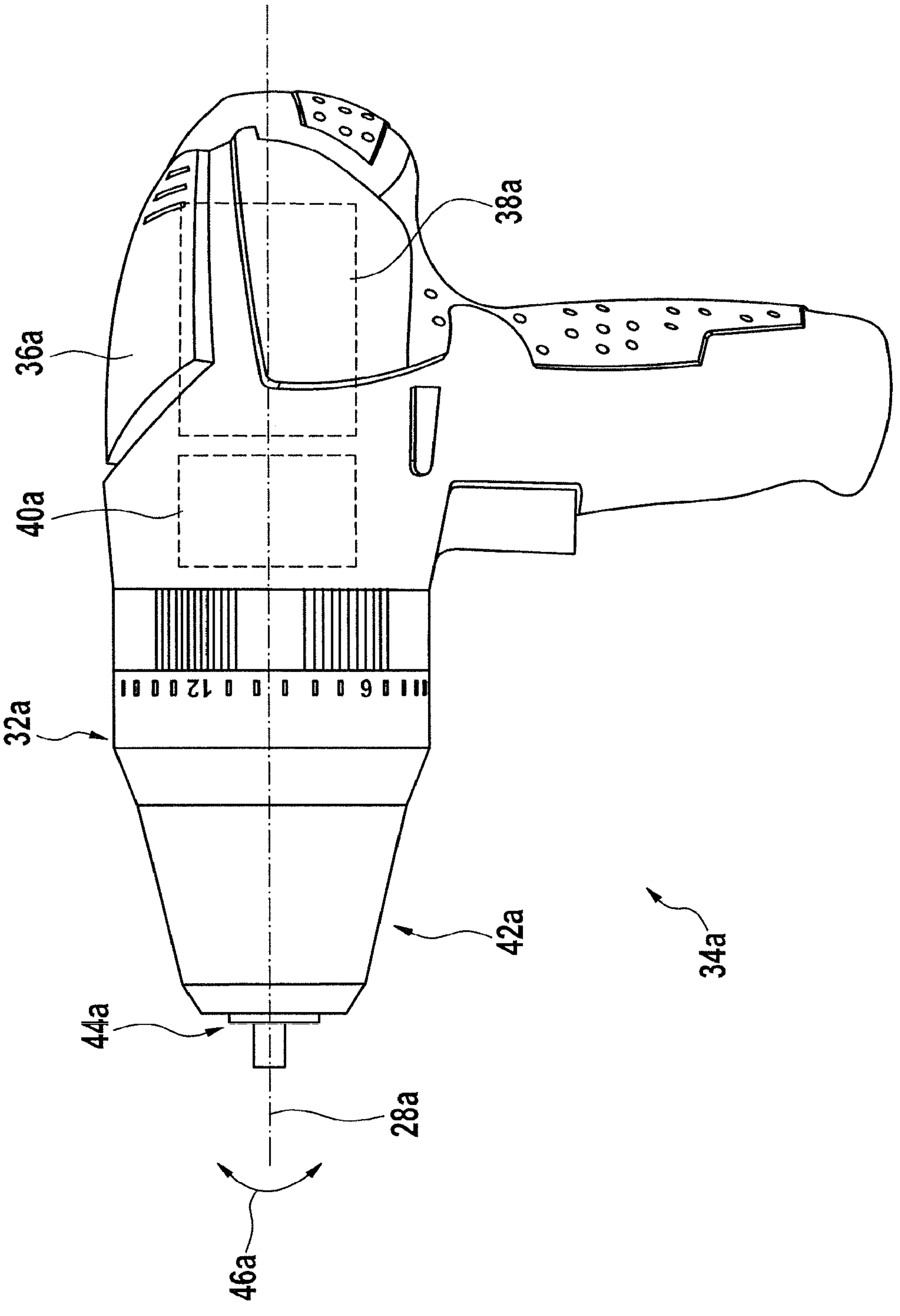
FIG. 1 shows a hand-held power tool equipped with a hand-held power tool device according to the invention.
Figure 2:
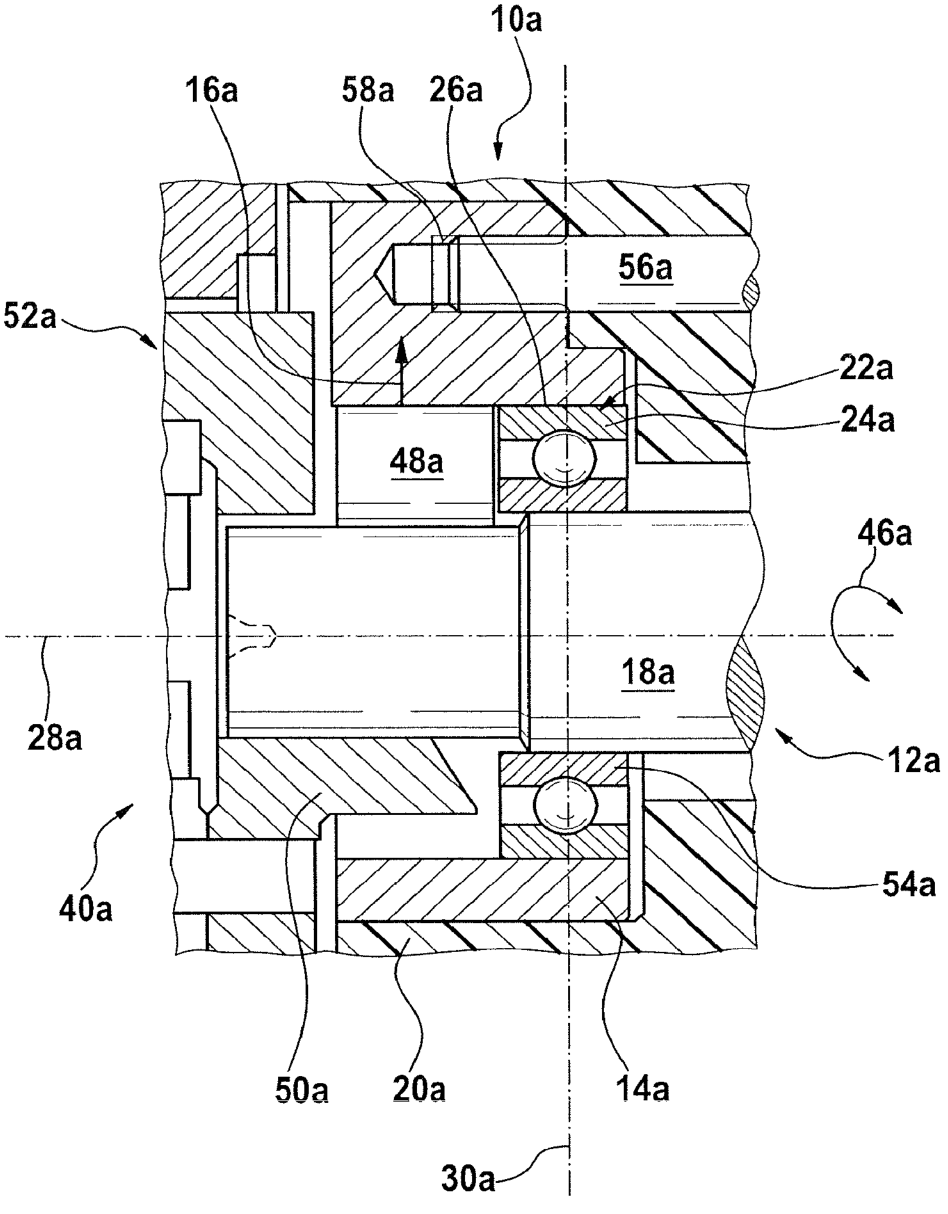
FIG. 2 shows a detail of a longitudinal section through the hand-held power tool from FIG. 1.

FIG. 1 schematically depicts a hand-held power tool embodied in the form of a cordless impact drill/screwdriver 34*a*, having a drive motor 38*a* that is accommodated in a machine housing 36*a* and is able to drive an output shaft 18*a* of an output device 12*a* via a planetary gear set 40*a* that is not depicted in detail (FIGS. 1 and 2). The output shaft 18*a* has a clamping chuck 42*a* fastened to it. The clamping chuck 42*a* has a clamping device 44*a* that can be actuated in order to fasten a tool in the rotation direction 46*a* around a rotation axis 28*a* of the output device 12*a* relative to the machine housing 36*a*.

The hand-held power tool also has a hand-held power tool device with a locking device 10*a* for locking the output shaft 18*a* of the output device 12*a* (FIG. 2). The locking device 10*a* is used to couple the output shaft 18*a* in a rotationally fixed fashion in relation to the machine housing 36*a* when the tool is being clamped and released by means of the clamping device 44*a*. The locking device 10*a* is automatically opened or more precisely stated, automatically releases the output shaft 18*a*, when a torque is transmitted from the drive motor 38*a* to the clamping chuck 42*a* and is automatically closed or more precisely stated, automatically immobilizes the output shaft 18*a*, when a torque is transmitted from the clamping chuck 42*a* to the drive motor 38*a*.

The locking device 10*a* includes a locking element 14*a*, which is embodied in the form of a clamping ring, for supporting radial clamping forces 16*a*. Inside the locking element 14*a*, clamping elements 48*a* are situated between the locking element 14*a* and the output shaft 18*a* and, in order to lock the output shaft 18*a* when a torque is transmitted from the clamping chuck 42*a* to the drive motor 38*a*, are moved in the circumference direction into tapering gaps, thus producing the radial clamping forces 16*a* and locking the output shaft 18*a* in the rotation direction 46*a*. The clamping elements 48*a* are embodied in the form of rollers. When a torque is transmitted from the drive motor 38*a* to the clamping chuck 42*a*, the clamping elements 48*a* are carried along by catch elements 50*a* of a catch device 52*a* so that the clamping elements 48*a* are prevented from jamming inside the locking element 14*a*. The catch device 52*a* is embodied of one piece with a planet carrier of the planetary gear seat 40*a*.

The locking element 14*a* is provided for fastening and axially securing components. The locking element 14*a* is affixed without play in the radial direction in a housing unit 20*a* of the machine housing 36*a*, which housing unit is manufactured out of plastic; in fact, the housing unit 20*a* is molded around the locking element 14*a*. The hand-held power tool device includes a pivot bearing unit 22*a* that is provided to support the output shaft 18*a* of the output device 12*a* at an end oriented toward the drive motor 38*a* and includes one of the components to be fastened, which is constituted by a bearing component 24*a*. The bearing component 24*a* and the locking element 14*a* are connected to each other by means of a press-fitted connection 26*a*. The bearing component 24*a* is constituted by an outer ring of a rolling bearing and is pressed-fitted into an inner circumference of the locking element 14*a*. The bearing component 24*a* and the locking element 14*a* arc situated in common planes 30*a* extending perpendicular to a rotation axis 28*a* of the pivot bearing unit 22*a*. The bearing component 24*a* is situated completely inside an axial region defined by the locking element 14*a*.

During operation, an inner bearing ring 54*a* of the pivot bearing unit 22*a* serves as an axial stop element for the clamping elements 48*a*, making it possible to advantageously prevent a relative movement between the clamping elements 48*a* and the inner bearing ring 54*a* and a resulting generation of heat. The inner bearing ring 54*a* is press-fitted onto the output shaft 18*a*. If the output shaft 18*a* is loaded in the direction toward the clamping elements 48*a*, then the inner bearing ring 54*a* is shifted slightly toward the clamping elements 48*a* in relation to the bearing component 24*a* so that the inner bearing ring 54*a* can advantageously function as a stop element.

The locking element 14*a* also serves to axially secure the output shaft 18*a* and an adjusting element 32*a* (FIG. 1). For this purpose, a securing means, not shown, which constitutes an axial stop for the output shaft 18*a* and an axial stop for the adjusting element 32*a*, is fastened to the locking element 14*a* by means of axial fastening means 56*a*. The fastening means 56*a* are constituted by screws that are screwed into internal threads 58*a* of the locking element 14*a*. The locking element 14*a* constitutes a screw flange.

Figure 3:
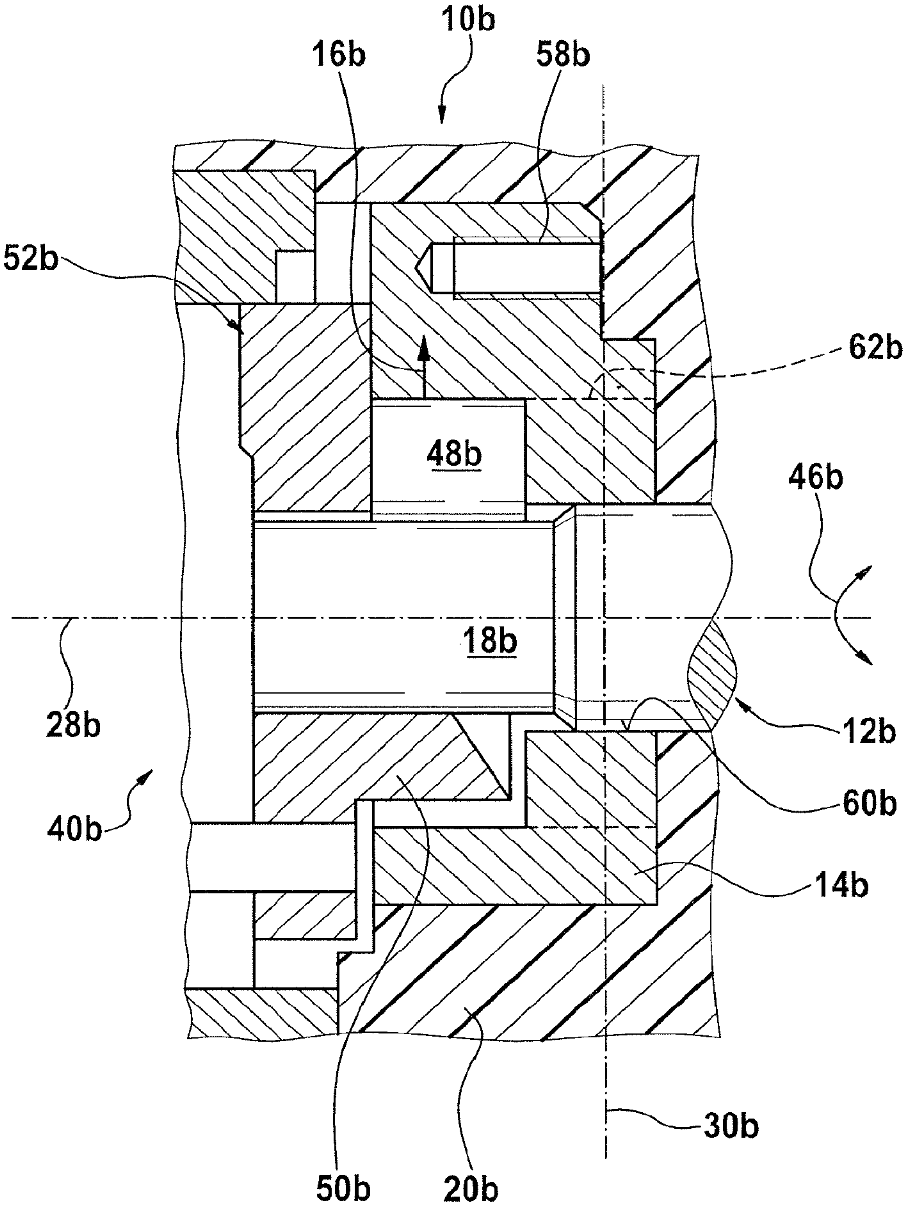
FIG. 3 shows a detail of a longitudinal section through an alternative hand-held power tool.

FIG. 3 shows an alternative exemplary embodiment. Components, features, and functions that remain the same have essentially been provided with the same reference numerals. To differentiate between the exemplary embodiments, however, the letters a and b have been added to their respective reference numerals. The description below is essentially limited to the differences as compared to the exemplary embodiment shown in FIGS. 1 and 2; with regard to components, features, and functions that remain the same, the reader is referred to the description of the exemplary embodiment shown in FIGS. 1 and 2.

FIG. 3 shows a hand-held power tool device with a locking element 14*b* that is provided for directly supporting an output shaft 18*b*. The locking element 14*b* constitutes a slide bearing surface 60*b* by means of which the locking element 14*b* directly contacts the output shaft 18*b*. The locking element 14*b* is manufactured out of a sintered material. Essentially, however, it is also conceivable for it to be made of any other material deemed suitable by the person skilled in the art.

It is also conceivable for a slide bearing 62*b* to be press-fitted into the locking element 14*b*, as indicated in FIG. 3.

The foregoing relates to preferred exemplary embodiments of the invention, it being understood that other variants and embodiments thereof are possible within the spirit and scope of the invention, the latter being defined by the appended claims.

The invention claimed is:

1. A hand-held power tool device, comprising:

an output device including an output shaft;

a locking device configured to lock the output shaft, the locking device including:

at least one locking element embodied as a clamping ring and configured to support at least one radial clamping force;

at least one clamping element embodied as a clamping roller; and at least one catch element configured to entrain the at least one clamping element; and a bearing unit configured to support the output shaft, the bearing unit including a bearing component, wherein the bearing component and the clamping ring are arranged in at least one first common plane extending perpendicular to a rotation axis of the output shaft; wherein the at least one clamping roller, the clamping ring, and the at least one catch element are arranged in at least one second common plane extending perpendicular to the rotation axis of the output shaft and parallel to the at least one first common plane.

2. The hand-held power tool device as recited in claim 1, wherein the bearing component is arranged completely within an axial extension of the clamping ring.

3. The hand-held power tool device as recited in claim 1, wherein the bearing component and the at least one clamping roller are arranged completely within an axial extension of the clamping ring.

4. The hand-held power tool device as recited in claim 1, wherein the at least one clamping roller and the clamping ring are arranged in at least one second common plane extending perpendicular to the rotation axis of the output shaft and parallel to the at least one first common plane.

5. The hand-held power tool device as recited in claim 1, wherein the bearing component is fixedly connected to an inner surface of the clamping ring.

6. The hand-held power tool device as recited in claim 1, wherein the bearing component is fixedly connected to the inner surface of the clamping ring by means of a press-fit connection.

7. The hand-held power tool device as recited in claim 1, wherein the bearing unit is embodied as a roller bearing, wherein the bearing component is embodied as an outer bearing ring of the roller bearing.

8. The hand-held power tool device as recited in claim 7, wherein the roller bearing includes an inner bearing ring which is directly supported on the output shaft.

9. The hand-held power tool device as recited in claim 8, wherein the inner bearing ring is fixedly connected to the output shaft by means of a press-fit connection.

10. The hand-held power tool device as recited in claim 8, wherein the inner bearing ring is configured to act as an axial stop element for the at least one clamping roller.

11. The hand-held power tool device as recited in claim 1, wherein the bearing unit is embodied as a slide bearing, wherein the bearing component includes a slide bearing surface which is directly supported on the output shaft.

12. The hand-held power tool device as recited in claim 11, wherein the bearing component is embodied in one piece with the clamping ring such that the clamping ring is directly supported on the output shaft.

13. The hand-held power tool device as recited in claim 11, wherein the bearing component is fixedly connected to the inner surface of the clamping ring.

14. The hand-held power tool device as recited in claim 11, wherein the bearing component is fixedly connected to the inner surface of the clamping ring by means of a press-fit connection.

15. The hand-held power tool device as recited in claim 1, wherein the bearing unit is configured to support the output shaft at an end oriented toward a drive motor.

16. The hand-held power tool device as recited in claim 1, wherein the at least one catch element is part of a catch device.

17. The hand-held power tool device as recited in claim 1, wherein the catch device is embodied in one piece with a planet carrier of a planetary gear.

18. The hand-held power tool device as recited in claim 1, wherein the at least one clamping roller is arranged between the clamping ring and the output shaft.

19. The hand-held power tool device as recited in claim 18, wherein the at least one clamping roller is directly supported on the output shaft.

20. The hand-held power tool device as recited in claim 1, wherein the at least one clamping roller is arranged adjacent to the bearing component in an axial direction of the output shaft.

21. The hand-held power tool device as recited in claim 1, wherein the at least one clamping ring is at least partially made of a sintered material.

22. The hand-held power tool device as recited in claim 1, further comprising:

a housing unit in which the at least one clamping ring is supported with a radial play of less than 0.1 mm.

23. The hand-held power tool device as recited in claim 1, further comprising:

a housing unit that is injection-molded around the clamping ring.

24. A hand-held power tool having a hand-held power tool device as recited in claim 1.

* * * * *